US011986285B2

(12) United States Patent
Hsiao et al.

(10) Patent No.: US 11,986,285 B2
(45) Date of Patent: May 21, 2024

(54) DISEASE DIAGNOSING METHOD AND DISEASE DIAGNOSING SYSTEM

(71) Applicant: National Taiwan University, Taipei (TW)

(72) Inventors: Hao-Ming Hsiao, Taipei (TW); Hsien-Li Kao, Taipei (TW); Mao-Shin Lin, Taipei (TW); Chung-Yuan Hsu, Taipei (TW)

(73) Assignee: National Taiwan University, Taipei (TW)

( * ) Notice: Subject to any disclaimer, the term of this patent is extended or adjusted under 35 U.S.C. 154(b) by 457 days.

(21) Appl. No.: 17/509,070

(22) Filed: Oct. 25, 2021

(65) Prior Publication Data

US 2022/0133171 A1 May 5, 2022

(30) Foreign Application Priority Data

Oct. 29, 2020 (TW) .................................. 109137647

(51) Int. Cl.
*A61B 5/103* (2006.01)
*A61B 5/00* (2006.01)
(Continued)

(52) U.S. Cl.
CPC .......... *A61B 5/1032* (2013.01); *A61B 5/0077* (2013.01); *A61B 5/0082* (2013.01);
(Continued)

(58) Field of Classification Search
CPC ....... A61B 3/0041; A61B 3/14; A61B 5/0064; A61B 5/0075; A61B 5/0077;
(Continued)

(56) References Cited

U.S. PATENT DOCUMENTS

| 10,395,370 B2 | 8/2019 | Hsiao et al. | |
| 2014/0177677 A1* | 6/2014 | Luo | H04B 1/7102 |
| | | | 375/131 |

(Continued)

FOREIGN PATENT DOCUMENTS

| CN | 105393252 | 3/2016 |
| CN | 103702014 | 2/2017 |

(Continued)

*Primary Examiner* — Negussie Worku
(74) *Attorney, Agent, or Firm* — JCIPRNET

(57) ABSTRACT

A disease diagnosing method and a disease diagnosing system are provided in the disclosure. The disease diagnosing method includes: obtaining continuous images of a body skin and generating a time domain signal according to an average pixel value of a region of interest in each frame of the continuous images; transforming the time domain signal to a frequency domain signal and combining the time domain signal and the frequency domain signal to a time frequency signal; retrieving multiple first features of a first high dimensional space of the time frequency signal to obtain multiple second features of a second high dimensional space; and use the second features as feature vectors to map to a high dimension feature space, and classifying the second features as one of the multiple categories of a disease corresponding to the region of interest in the body skin according to a hyperplane of the high dimension feature space.

16 Claims, 6 Drawing Sheets

(51) Int. Cl.
*A61B 5/0205* (2006.01)
*A61B 5/026* (2006.01)
*G06T 7/00* (2017.01)

(52) U.S. Cl.
CPC ........ *A61B 5/02055* (2013.01); *A61B 5/0261* (2013.01); *A61B 5/445* (2013.01); *A61B 5/4842* (2013.01); *A61B 5/4848* (2013.01); *A61B 5/726* (2013.01); *A61B 5/7264* (2013.01); *G06T 7/0012* (2013.01); *G06T 2207/30088* (2013.01); *G06T 2207/30201* (2013.01)

(58) Field of Classification Search
CPC ... A61B 5/02007; A61B 5/026; A61B 5/0261; A61B 5/14551; A61B 5/441; A61B 5/443; A61B 5/445; A61B 5/7264; A61B 5/7267; G06T 2207/10016; G06T 2207/10024; G06T 2207/20016; G06T 2207/30076; G06T 7/0016; G06T 7/33; G06V 10/60; G16H 50/20; H04N 23/51; H04N 23/635; H04N 5/2621; H04N 5/265
USPC ........................................................ 382/128
See application file for complete search history.

(56) References Cited

U.S. PATENT DOCUMENTS

| | | | |
|---|---|---|---|
| 2014/0313303 A1* | 10/2014 | Davis ...................... | A61B 5/68 348/77 |
| 2016/0078622 A1* | 3/2016 | Hsiao ...................... | G06T 7/33 348/78 |
| 2016/0171684 A1* | 6/2016 | De Haan ............... | G06T 7/0012 382/103 |
| 2019/0188851 A1* | 6/2019 | Zouridakis ............ | G06T 7/0012 |
| 2020/0138360 A1 | 5/2020 | Fan et al. | |
| 2020/0138369 A1* | 5/2020 | Shimuta ................. | G16H 20/30 |
| 2021/0072255 A1* | 3/2021 | Farokhzad ............... | G06N 3/04 |
| 2021/0199643 A1* | 7/2021 | Bharitkar ............. | G01N 33/497 |
| 2022/0240783 A1* | 8/2022 | Fan ........................ | A61B 5/441 |

FOREIGN PATENT DOCUMENTS

| | | |
|---|---|---|
| CN | 111028206 | 4/2020 |
| TW | I524878 | 3/2016 |
| TW | M586599 | 11/2019 |
| TW | 202005609 | 2/2020 |

\* cited by examiner

DISEASE DIAGNOSING METHOD AND DISEASE DIAGNOSING SYSTEM

CROSS-REFERENCE TO RELATED APPLICATION

This application claims the priority benefit of Taiwan application serial no. 109137647, filed on Oct. 29, 2020. The entirety of the above-mentioned patent application is hereby incorporated by reference herein and made a part of this specification.

BACKGROUND

Technical Field

The disclosure relates to a disease diagnosing method and a disease diagnosing system, and in particular, to a disease diagnosing method and a disease diagnosing system that obtain physiological information related to the disease according to the color change of a body skin.

Description of Related Art

When a patient develops a disease (e.g., arrhythmia or carotid artery stenosis, etc.), the body surface skin of the patient has very subtle color changes unrecognizable by naked eyes due to changes in blood flow or temperature. When the patient wants to confirm the condition, he or she can only go to a hospital for a further examination, which is laborious and time-consuming. Therefore, how to provide a fast and convenient disease diagnosing method is a goal for those skilled in the art.

SUMMARY

In this regard, the disclosure provides a disease diagnosing method and a disease diagnosing system to obtain physiological information related to the disease according to the color change of the body skin.

The disclosure provides a disease diagnosing method including the following steps. Obtain continuous images of a body skin and generate a time domain signal according to an average pixel value of a region of interest in each frame of the continuous images. Transform the time domain signal to a frequency domain signal and combine the time domain signal and the frequency domain signal to a time frequency signal. Retrieve multiple first features of a first high dimensional space of the time frequency signal and obtain multiple second features of a second high dimensional space according to the first features. The dimension of the first high dimensional space is greater than the dimension of the second dimensional space. In addition, use the second features as feature vectors to map to a high dimension feature space, and classify the second features as one of the multiple categories of the disease corresponding to the region of interest in the body skin according to a hyperplane of the high dimension feature space.

The disclosure provides a disease diagnosing system including an image sensor and a processor coupled to the image sensor. The image sensor obtains continuous images of a body skin, and the processor generates a time domain signal according to an average pixel value of a region of interest in each frame of the continuous images. The processor transforms the time domain signal to a frequency domain signal and combines the time domain signal and the frequency domain signal to a time frequency signal. The processor retrieves multiple first features of a first high dimensional space of the time frequency signal, and obtains multiple second features of a second high dimensional space according to the first features. The dimension of the first high dimensional space is greater than the dimension of the second high dimensional space. The processor uses the second features as feature vectors to map to a high dimensional feature space, and classifies the second features as one of multiple categories of the disease corresponding to the region of interest in the body skin according to a hyperplane of the high dimensional feature space.

Based on the above, with the disease diagnosing method and the disease diagnosing system in the disclosure, the skin images of a patient are obtained and a time domain signal is generated according to the pixel value of the skin images. A time frequency signal is obtained according to the time domain signal, and then a high dimensional first feature is obtained to perform the operation of reducing the dimension to obtain a second feature with a lower dimension. The second feature is mapped to another high dimensional feature space and a hyperplane classifies the second feature as one of the multiple categories of the disease. Therefore, the disease diagnosing method and the disease diagnosing system in the disclosure are capable of determining whether the patient has a disease or not or determining the severity of the disease of the patient in a fast and convenient manner.

DESCRIPTION OF THE EMBODIMENTS

Figure 1:
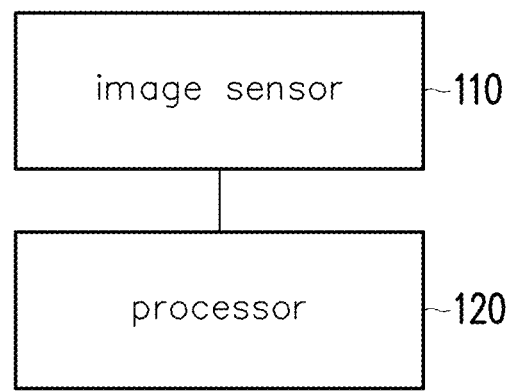
FIG. 1 is a block view of a disease diagnosing system according to an embodiment of the disclosure.

FIG. 1 is a block view of a disease diagnosing system according to an embodiment of the disclosure.

Refer to FIG. 1. The disease diagnosing system of an embodiment in the disclosure includes an image sensor 110 and a processor 120. The image sensor 110 is coupled to the processor 120. The image sensor 110 retrieves the continuous images of a body skin, and the processor 120 determines the physiological information of the patient from the continuous images, such as heart rate information, having a disease or not, the severity of the disease, etc. In one embodiment, the image sensor 110 and the processor 120 may be disposed in an electronic device (e.g., a smart phone or a tablet computer, etc.), so that the user obtains his/her physiological information directly through the electronic device. In another embodiment, the image sensor 110 may be disposed in an electronic device (e.g., a smart phone or a tablet computer, etc.) and the processor 120 may be disposed in a server. The user retrieves the continuous images of the body skin through the electronic device and send the continuous images to the server for analysis, and the server returns the physiological information determined through the continuous images to the electronic device of the user. The implementation methods of the image sensor 110 and the processor 120 in the disclosure are not limited thereto. The image sensor 110 may include a complementary metal-oxide-semiconductor (CMOS) image sensor, a charge-coupled device (CCD) image sensor, or other similar image sensor elements. The processor 120 may be a central processing unit (CPU), or other programmable general-purpose or special-purpose microprocessors, a digital signal processor (DSP), a programmable controller, an application specific integrated circuit (ASIC), or other similar apparatuses or a combination thereof.

Figure 2:
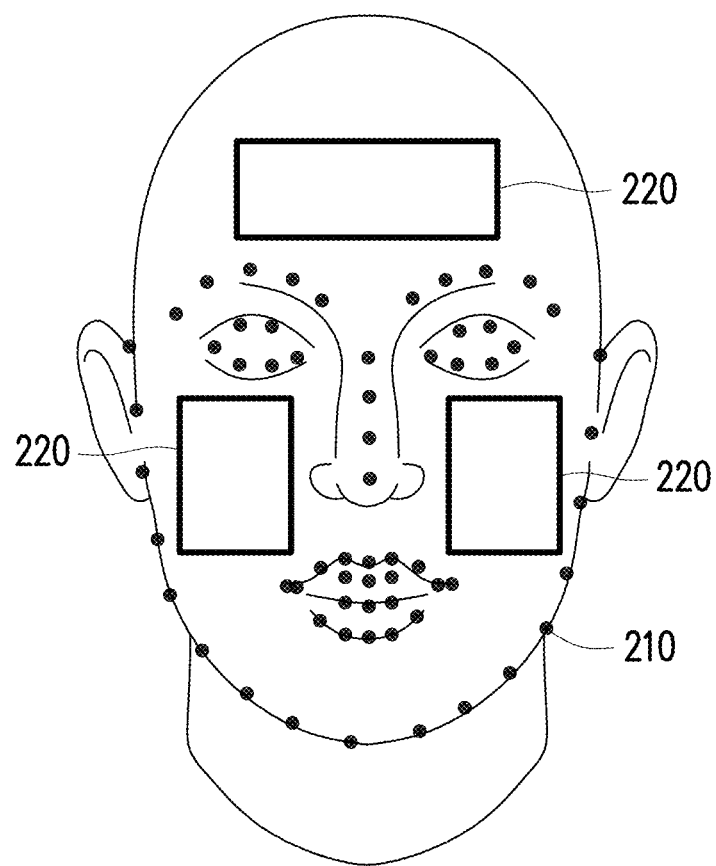
FIG. 2 is a schematic view of feature points and regions of interest in a body skin according to an embodiment of the disclosure.

In an embodiment, the image sensor 110 obtains the continuous images of a body skin, and the processor 120 generates a time domain signal according to an average pixel value of a region of interest in each frame of the continuous images. FIG. 2 is a schematic view of feature points and regions of interest in a body skin according to an embodiment of the disclosure. Refer to FIG. 2. In the continuous images, the processor 120 uses the facial feature recognition algorithm to detect multiple feature points 210 which are the positions of the five sense organs on a human face such as eyes, a nose, a mouth, ears, facial contours, etc. in the first frame of the images. The feature points 210 are adapted to locate a specific position of the face in the continuous images for subsequent tracking and analysis. Then, the processor 120 uses the feature point tracking algorithm to track and record the coordinates of the feature points 210 throughout the continuous images. The feature point tracking algorithm performs a pixel value distribution comparison between each frame and its adjacent frame to determine the position of the facial feature in the current frame. With the feature point tracking algorithm, the processor 120 records the corresponding positions of the same feature points in the continuous images. For example, in the first image, if the processor 120 detects that there are specific feature points at the end of an eye, then in the subsequent continuous images, even if there is slight movement or shaking of the human face, the feature point tracking algorithm is still capable of clearly marking the coordinates of the specific feature points at the end of the eye in the current frame of the image. The region of interest in the disclosure is not limited to human faces. The region of interest may also be the skin of fingers or toes (adapted to determine whether the peripheral circulation is good) or the skin of wrists (adapted to determine whether the arteriovenous tube is blocked) and so on.

The processor 120 marks multiple feature points 210 on the face and tracks the feature points 210 to obtain the coordinates of the feature points 210 at any time point in the continuous images. Then, the processor 120 uses the position of the feature points 210 to define the coordinate of a region of interest 220 according to requirements. Finally, the processor 120 generates a one-dimensional time domain signal according to the average pixel value of the region of interest 220 in each frame of the continuous images.

After obtaining the time domain signal, the processor 120 retrieves the signal in the time domain signal that meets the frequency range of interest through the filter of the time domain. The filter removes the unwanted specific frequency part with the multiplication of a period of signal and the signal of the filter. For example, a high-pass filter may allow the original signal to output a signal containing high frequency components after passing through the filter, and most of the low frequency components in the original signal is removed after being multiplied by the signal of the filter. The target signal analyzed corresponds to the skin parameters of the face, neck or other parts, so the filter is capable of filtering out the reasonable frequency range (e.g., the frequency range ranging from 0 Hz to 10 Hz) of most physiological signals. In one embodiment, the processor 120 may transform the time domain signal to the frequency domain signal and combine the time domain signal and the frequency domain signal to a time frequency signal, and use the two-dimensional time frequency signal as the input layer of the neural network (e.g., the convolutional neural network) and retrieve the function of the features of the high dimensional space (i.e., the first high dimensional space) through the first few layers of the neural network to retrieve the high dimensional features of the time frequency signal (or referred to the first feature).

Figure 3:
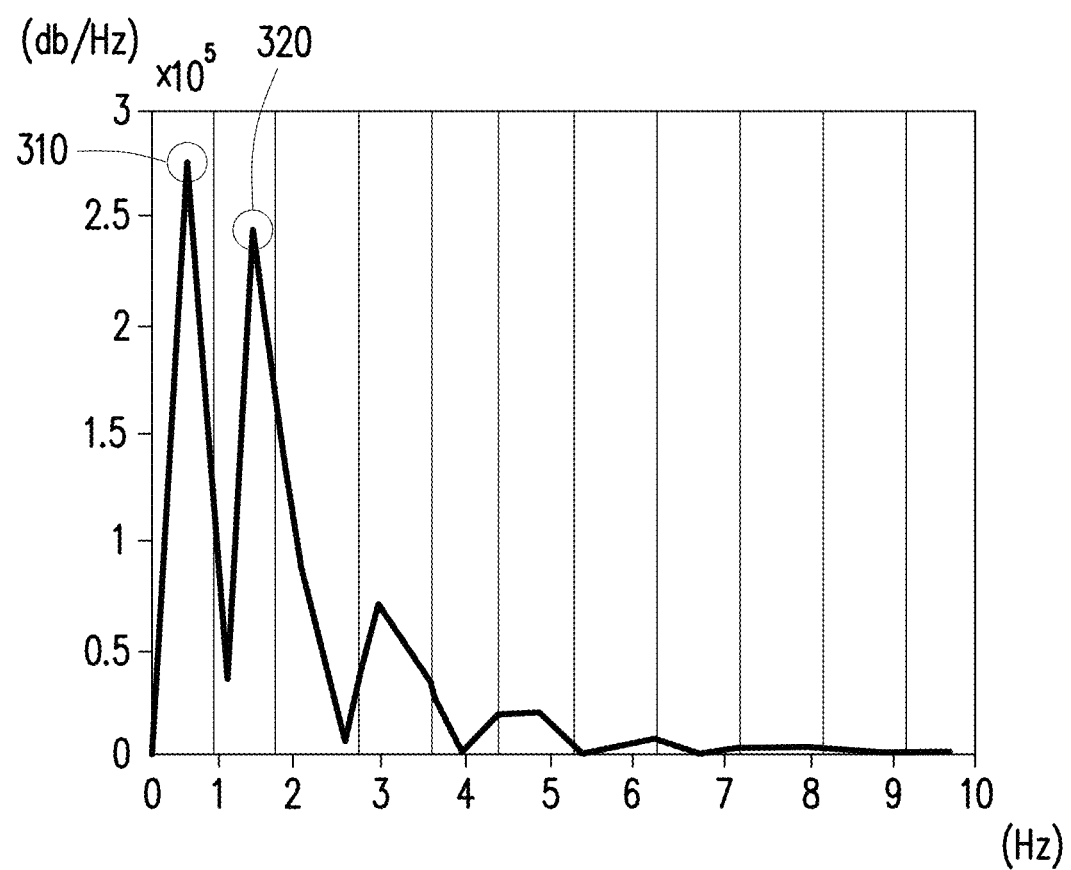
FIG. 3 is a schematic view of the calculation of the energy ratio of segmented frequency bands according to an embodiment of the disclosure.

Although the embodiment illustrates how to retrieve the high dimensional features of the time frequency signal with a neural network, the disclosure is not limited thereto. In another embodiment, the processor 120 analyzes multiple parameters of the signal in the time domain and/or frequency domain by means of mathematical conversion (or statistical model), and uses the parameters obtained from the mathematical conversion as the high dimensional features of the signal. The processor 120 may use a statistical model to obtain statistical parameters (e.g., parameters that represents the dispersion degree of the signal distribution, such as mean, standard deviation, and variance) of the signal in the time domain or the frequency domain, and add the statistical parameters to the high dimensional features. The processor 120 may also fit the time domain signal to a Gaussian function to adjust multiple parameters so that the Gaussian waveform substantially equals to the waveform of the time domain signal, and add the adjusted parameters to the high dimensional features. After the processor 120 transforms the time domain signal to the frequency domain with Fourier transform, the frequency value corresponding to the highest point of the energy distribution of the frequency domain signal, the energy ratio between multiple frequency bands segmented from the frequency domain signal, and the average energy of the frequency domain signal are added to the high dimensional features. FIG. 3 is a schematic view of the calculation of the energy ratio of segmented frequency bands according to an embodiment of the disclosure. Refer to FIG. 3. After the frequency domain signal is segmented into frequency bands, the power spectral density (PSD) corresponding to multiple frequency bands is obtained. The signal 310 ranging from frequency 0 to 1 has the highest power spectral density, and the signal 320 ranging from frequency 1 to 2 has the second highest power spectral density. The signal 310 may be a signal corresponding to a breath, and the signal 320 may be a signal corresponding to a heart rate. The processor 120 also retrieves the high dimensional features from the time frequency signal through a time frequency analysis algorithm. Time frequency analysis algorithms include wavelet transform and Hilbert-Huang transform (HHT). With the statistical model, the processor 120 outputs the physiological values corresponding to the initial time domain signal, such as heart rate values, heart rate variability, and values of the breath per minute. For example, when the frequency in the time frequency distribution graph is maintained at 1.2 Hz at each time, the processor 120 determines that the heartbeat of the subject is 72 beats per minute.

Note that the processor 120 may retrieve the high dimensional features first with a statistical model and then perform the subsequent operations. When the accuracy of the final diagnosis of the disease is greater than the threshold value, the neural network is not adapted to retrieve the high dimensional features. However, when the statistical model is used to retrieve the high dimensional features, the accuracy of the final diagnosis of the disease is less than the threshold value (e.g., the specificity is less than 99%), the processor 120 then retrieves the high dimensional features with the neural network and performs the subsequent operations.

After retrieving the high dimensional features, the processor 120 first reduces the dimension of the high dimensional features and then classifies them. Two major requirements need to be met to reduce dimensions. The first requirement is to reduce the dimension to the extent that processor 120 is capable of performing analyses in a highly efficient manner. If the dimension is not reduced enough, the efficiency of the calculation of the processor 120 is still low and the calculation process is still time-consuming. The second requirement is that after reducing the dimensions, the remaining few dimensions still have to represent the signal. In other words, the remaining few dimensions still have the ability to represent the performance or the characteristics of the signal. In one embodiment, the processor 120 performs the principal components analysis (PCA) algorithm to reduce the dimension of the high dimensional features (or referred to the first features) of the first high dimensional space to obtain the low dimensional features (or referred to the second features) of the second high dimensional space. The dimension of the first high dimensional space is greater than the dimension of the second high dimensional space. The principal component analysis algorithm is adapted to retrieve useful information contained in a data set that contains many variables and are related to one another, and when reducing the dimension of the original data set, the feature that contributes the most to the variance in the data is maintained. The principal component analysis gets the principal components in the data, that is, the new combination of orthogonal variables or the feature vectors of the data. The processor 120 multiplies the feature coefficient corresponding to the feature vector with the original data matrix to obtain the feature result of the principal component analysis.

Figure 4:
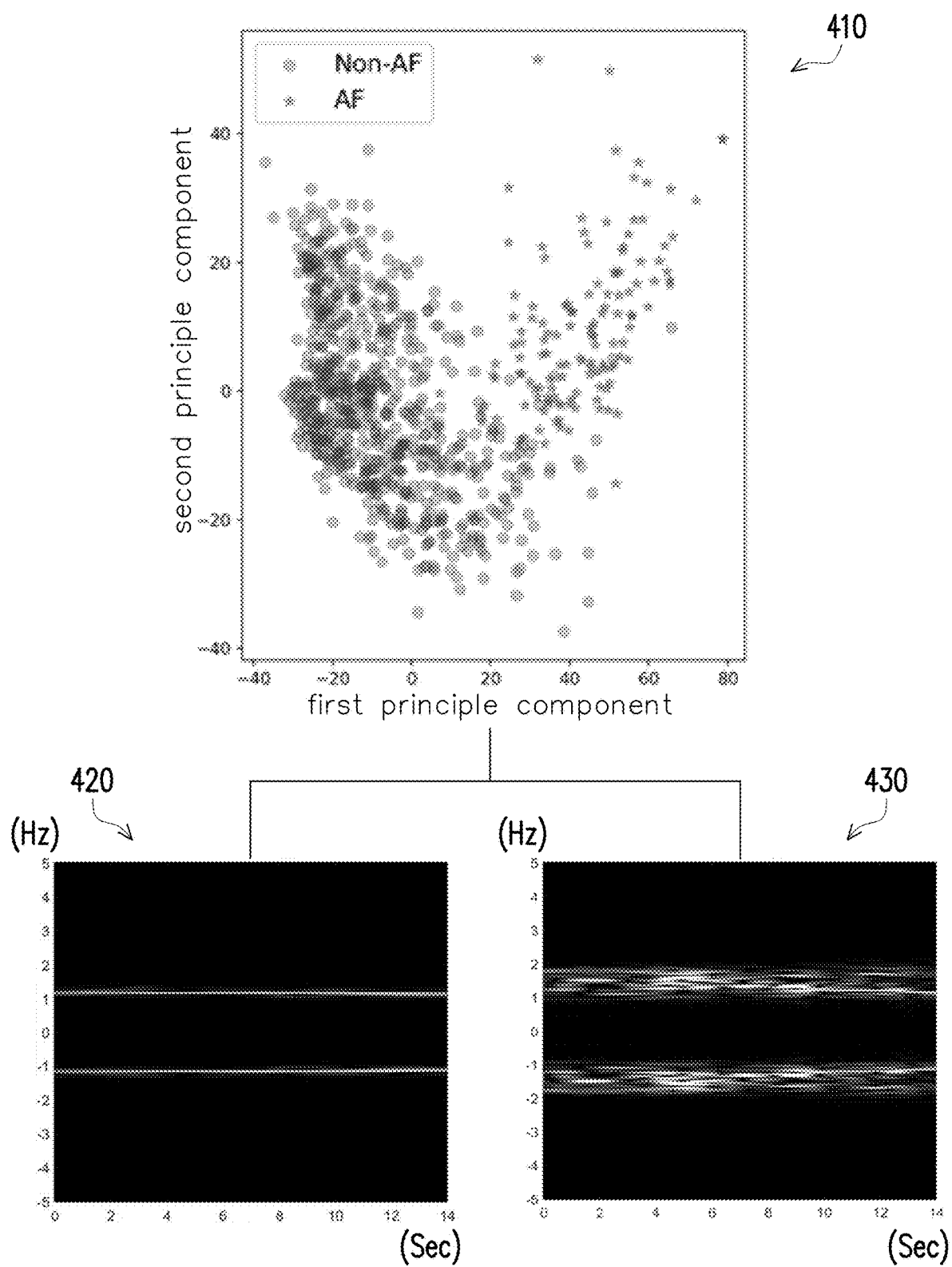
FIG. 4 is a schematic view of a two-dimensional result of principal component analysis and time frequency analysis of a data set with or without atrial fibrillation according to an embodiment of the disclosure.

FIG. 4 is a schematic view of a two-dimensional result of principal component analysis and time frequency analysis of a data set with or without atrial fibrillation according to an embodiment of the disclosure. Refer to FIG. 4. Chart 410 shows after the use of a data set of known atrial fibrillation (AF) to retrieve high dimensional features, the operation of reducing the dimension is performed, and then information is obtained from the two most important feature dimensions of the principal component analysis. Chart 420 is a two-dimensional result of a signal of a person with a normal heart rhythm after the time frequency analysis. Chart 430 is a two-dimensional result of a signal of a patient with arrhythmia after the time frequency domain analysis. Chart 420 and chart 430 show that the patient with arrhythmia has drastic and irregular changes of the signal frequency distribution with time, while those with normal heart rhythms have no significant changes and the signal frequency distribution remains very stable.

In one embodiment, after the low dimensional feature (or referred to the second feature) of which the dimension has been reduced is obtained, the processor 120 uses the low dimensional feature as a feature vector to map to the high dimensional feature space through the kernel function of the classifier, and classifies the low dimensional feature into one of the multiple categories of the disease corresponding to the region of interest in the body skin according to a hyperplane in the high dimensional feature space (i.e., the hyperplane searched in the high dimensional feature space using the core function). The classifier is, for example, a support vector machine (SVM). The categories of the disease classified through the hyperplane include the category with disease and the category without disease. The disease includes arrhythmia, abnormal biological temperature, and shock. The categories of the disease classified through the hyperplane may also include multiple severity classes of the disease. The disease includes carotid artery stenosis, arteriovenous tube obstruction, growth status of transplanted skin tissue, drug monitoring in which the drugs affect blood flow and temperature (i.e., the operation of drugs that affect blood flow and temperature is determined through changes in skin color), monitoring of blood peripheral circulation, and the depth and the area of tissue burns and frostbite.

Figure 5:
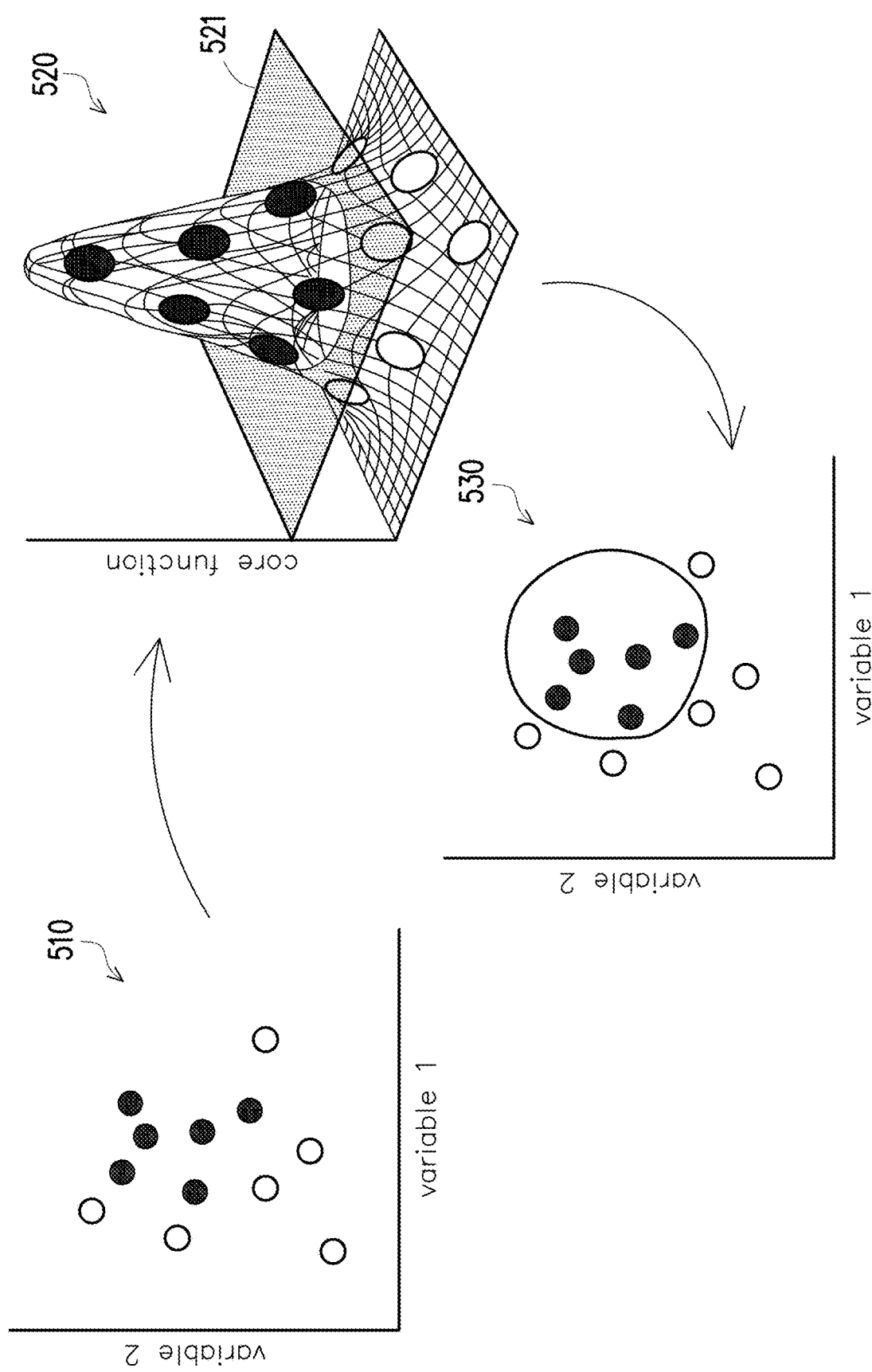
FIG. 5 is a schematic view of a classifier according to an embodiment of the disclosure.

FIG. 5 is a schematic view of a classifier according to an embodiment of the disclosure. Refer to FIG. 5. Chart 510 shows raw data that cannot be classified. Chart 520 shows that the original data are mapped to the high dimensional feature space through the core function and classified through a hyperplane 521, as shown in chart 530. In other words, the classifier searches for the band-shaped region formed by the hyperplane that accurately predicts the distribution of the data in a high dimensional feature space to solve the original dimensional nonlinear fitting problem. The classifier is capable of finding a tool for optimizing the cutting plane. With the cutting plane, the categories of multi-dimensional feature points are distinguished, and the cutting plane is used to predict the categories of unknown data.

Figure 6:
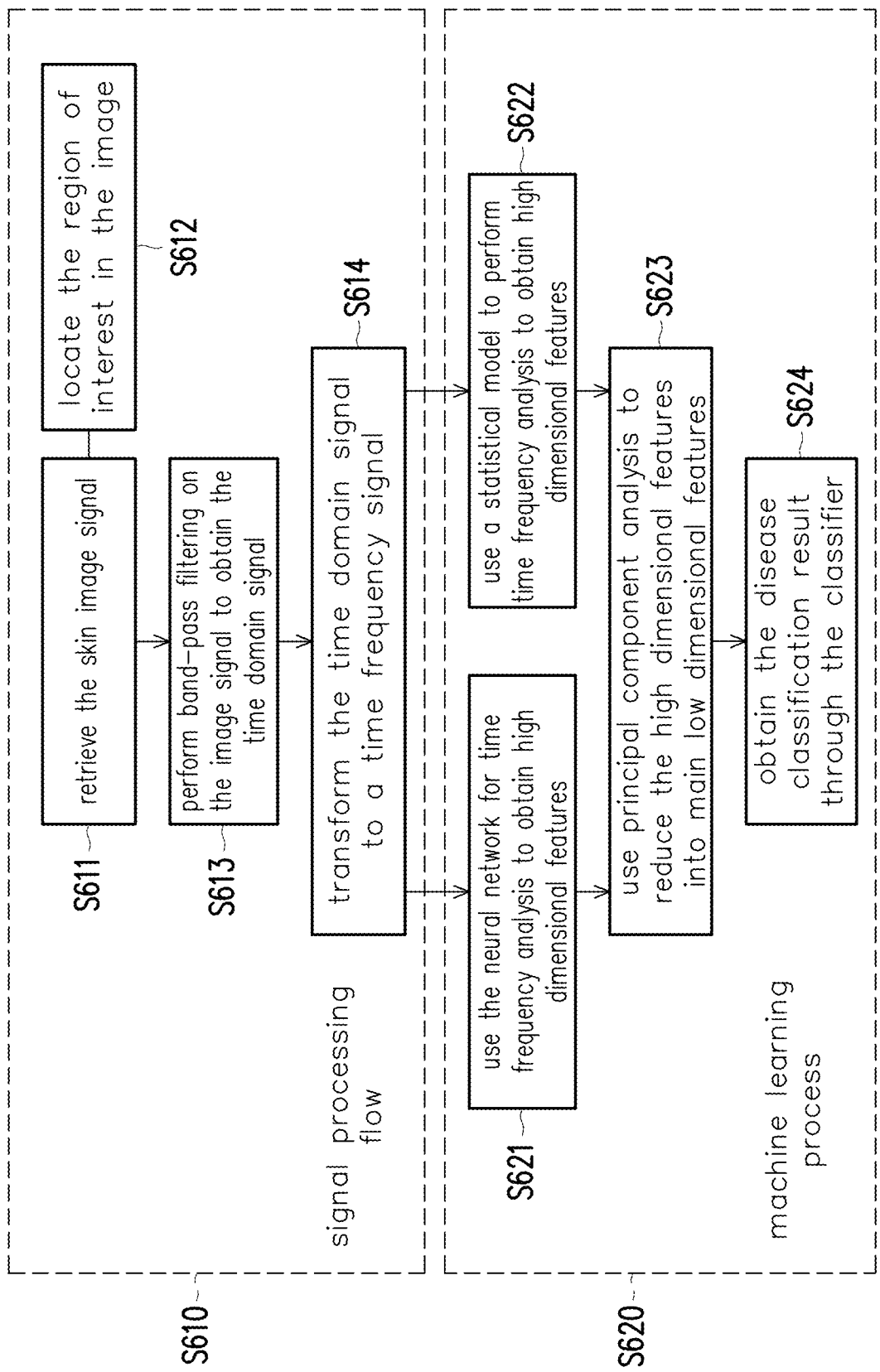
FIG. 6 is a flowchart of a disease diagnosing method according to an embodiment of the disclosure.

FIG. 6 is a flowchart of a disease diagnosing method according to an embodiment of the disclosure.

Refer to FIG. 6. The disease diagnosing method of an embodiment in the disclosure may include a signal processing flow S610 and a machine learning process S620.

In step S611, a skin image signal is retrieved.

In step S612, the region of interest in the image is located.

In step S613, a band-pass filtering is performed on the image signal to obtain a time domain signal.

In step S614, the time domain signal is transformed to the time frequency signal.

In step S621, the neural network is used for time frequency analysis to obtain high dimensional features.

In step S622, a statistical model is adapted to perform time frequency analysis to obtain high dimensional features.

In step S623, principal component analysis is adapted to reduce the high dimensional features into main low dimensional features.

In step S624, the disease classification result is obtained through the classifier.

Figure 7:
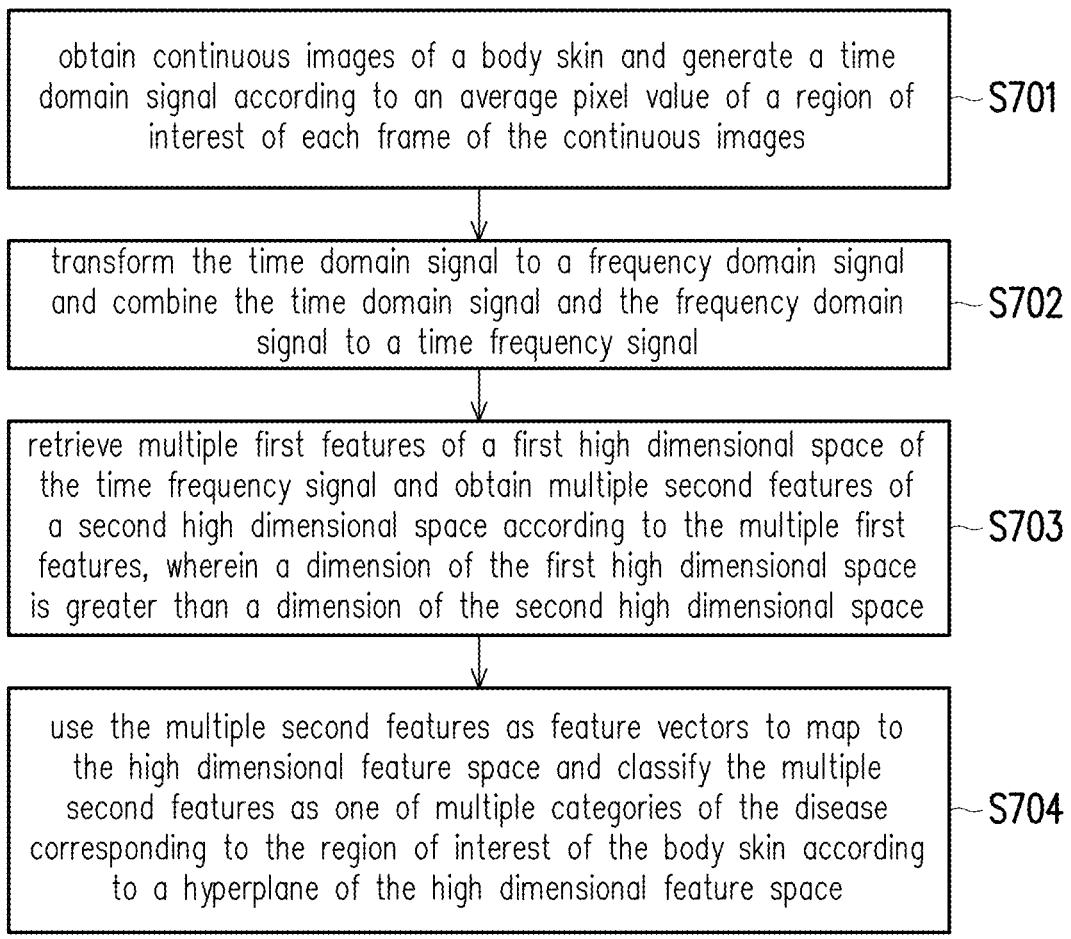
FIG. 7 is a flowchart of a disease diagnosing method according to another embodiment of the disclosure.

FIG. 7 is a flowchart of a disease diagnosing method according to another embodiment of the disclosure.

Refer to FIG. 7. In step S701, continuous images of a body skin are obtained, and a time domain signal is generated according to an average pixel value of a region of interest in each frame of the continuous images.

In step S702, the time domain signal is transformed to a frequency domain signal, and the time domain signal and the frequency domain signal are combined to a time frequency signal.

In step S703, multiple first features of a first high dimensional space of the time frequency signal are retrieved, and multiple second features of a second high dimensional space are obtained according to the first features, wherein the dimension of the first high dimensional space is greater than the dimension of the second high dimensional space.

In step S704, the second features are used as feature vectors to map to a high dimensional feature space, and the second features are classified as one of the multiple categories of the disease corresponding to the region of interest in the body skin according to a hyperplane of the high dimensional feature space.

Based on the above, with the disease diagnosing method and the disease diagnosing system in the disclosure, the skin images of a patient are obtained and a time domain signal is generated according to the pixel value of the skin images. A time frequency signal is obtained according to the time domain signal, and then a high dimensional first feature is obtained to perform the operation of reducing the dimension to obtain a second feature with a lower dimension. The second feature is mapped to another high dimensional feature space and a hyperplane classifies the second feature as one of the multiple categories of the disease. Therefore, the disease diagnosing method and the disease diagnosing system in the disclosure are capable of determining whether the patient has a disease or not or determining the severity of the disease of the patient in a fast and convenient manner.

Although the disclosure has been described with reference to the above embodiments, it will be apparent to one of ordinary skill in the art that modifications to the described embodiments may be made without departing from the spirit of the disclosure. Accordingly, the scope of the disclosure will be defined by the attached claims and their equivalents and not by the above detailed descriptions.

What is claimed is:

1. A disease diagnosing method adapted to obtain physiological information related to a disease according to a color change of a body skin, wherein the disease diagnosing method comprises:
   obtaining continuous images of the body skin, and generating a time domain signal according to an average pixel value of a region of interest in each frame of the continuous images;
   transforming the time domain signal to a frequency domain signal, and combining the time domain signal and the frequency domain signal to a time frequency signal;
   retrieving a plurality of first features of a first high dimensional space of the time frequency signal to obtain a plurality of second features of a second high dimensional space according to the plurality of the first features, wherein a dimension of the first high dimensional space is greater than a dimension of the second high dimensional space; and
   using the plurality of the second features as feature vectors to map to a high dimensional feature space, and classifying the plurality of the second features as one of a plurality of categories of the disease corresponding to the region of interest in the body skin according to a hyperplane of the high dimensional feature space.

2. The disease diagnosing method according to claim 1, wherein the plurality of the categories of the disease classified through the hyperplane comprise the category with disease and the category without the disease, and the category with the disease comprises arrhythmia, abnormal biological body temperature, and shock.

3. The disease diagnosing method according to claim 1, wherein the plurality of the categories of the disease classified through the hyperplane comprise a plurality of severity classes of the disease, wherein the disease comprises carotid artery stenosis, arteriovenous tube obstruction, growth status of transplanted skin tissue, drug monitoring in which drugs affects blood flow and temperature, monitoring of peripheral blood circulation, and a depth and an area of tissue burns and frostbite.

4. The disease diagnosing method according to claim 1, further comprising: tracking a plurality of feature points in the continuous images and obtaining the region of interest according to positions of the plurality of the feature points in the continuous images.

5. The disease diagnosing method according to claim 1, further comprising: retaining a signal in a frequency range of the time domain signal through a filter and removing other signals not in the frequency range, wherein the frequency range ranges from 0 Hz to 10 Hz.

6. The disease diagnosing method according to claim 1, further comprising: inputting the time frequency signal into a neural network and obtaining the plurality of the first features from the neural network, wherein the neural network comprises a convolutional neural network.

7. The disease diagnosing method according to claim 1, wherein the step of retrieving the plurality of the first features of the first high dimensional space of the time frequency signal comprises:
   calculating a statistical parameter of the time domain signal or that of the frequency domain signal to be added into the plurality of the first features;
   fitting the time domain signal to a Gaussian function, adjusting a plurality of parameters so that a Gaussian waveform substantially equals to a waveform of the time domain signal, and adding the plurality of the parameters to the plurality of the first features;
   adding a frequency value, an energy ratio between a plurality of frequency bands segmented from the frequency domain signal, and an average energy of the frequency domain signal corresponding to a highest point of an energy distribution of the frequency domain signal into the plurality of the first features; and
   retrieving the plurality of the first features from the time frequency signal through a time frequency analysis algorithm, wherein the time frequency analysis algorithm comprises a wavelet transform and a Hilbert-Huang transform.

8. The disease diagnosing method according to claim 1, wherein a core function is adapted to map the plurality of the second features to the high dimensional feature space, and the core function is adapted to search a hyperplane in the high dimensional feature space to classify the plurality of the second features into the plurality of the categories.

9. A disease diagnosing system comprising:
   an image sensor; and
   a processor coupled to the image sensor,
   wherein the image sensor obtains continuous images of a body skin, and the processor generates a time domain signal according to an average pixel value of a region of interest in each frame of the continuous images;
   the processor transforms the time domain signal to a frequency domain signal and combines the time domain signal and the frequency domain signal to a time frequency signal;
   the processor retrieves a plurality of first features of a first high dimensional space of the time frequency signal, and obtains a plurality of second features of a second high dimensional space according to the plurality of the first features, wherein a dimension of the first high dimensional space is greater than a dimension of the second high dimensional space; and the processor uses the plurality of the second features as feature vectors to map to a high dimensional feature space, and classifies the plurality of the second features as one of a plurality of categories of the disease corresponding to the region of interest in the body skin according to a hyperplane of the high dimensional feature space.

10. The disease diagnosing system according to claim 9, wherein the plurality of the categories of the disease classified through the hyperplane comprise the category with disease and the category without the disease, and the category with the disease comprises arrhythmia, abnormal biological body temperature, and shock.

11. The disease diagnosing system according to claim 9, wherein the plurality of the categories of the disease classified through the hyperplane comprise a plurality of severity classes of the disease, wherein the disease comprises carotid artery stenosis, arteriovenous tube obstruction, growth status of transplanted skin tissue, drug monitoring in which drugs affects blood flow and temperature, monitoring of peripheral blood circulation, and a depth and an area of tissue burns and frostbite.

12. The disease diagnosing system according to claim 9, wherein the processor tracks a plurality of feature points in the continuous images and obtains the region of interest according to positions of the plurality of the feature points in the continuous images.

13. The disease diagnosing system according to claim 9, wherein the processor retains a signal in a frequency range of the time domain signal through a filter and removes other signals not in the frequency range, wherein the frequency range ranges from 0 Hz to 10 Hz.

14. The disease diagnosing system according to claim 9, wherein the processor inputs the time frequency signal into a neural network and obtains the plurality of the first features from the neural network, wherein the neural network comprises a convolutional neural network.

15. The disease diagnosing system according to claim 9, wherein the processor calculates a statistical parameter of the time domain signal or that of the frequency domain signal to be added into the plurality of the first features;
fits the time domain signal to a Gaussian function, adjusts a plurality of parameters so that a Gaussian waveform substantially equals to a waveform of the time domain signal, and adds the plurality of the parameters to the plurality of the first features;
adds a frequency value, an energy ratio between a plurality of frequency bands segmented from the frequency domain signal, and an average energy of the frequency domain signal corresponding to a highest point of an energy distribution of the frequency domain signal into the plurality of the first features; and
retrieves the plurality of the first features from the time frequency signal through a time frequency analysis algorithm, wherein the time frequency analysis algorithm comprises a wavelet transform and a Hilbert-Huang transform.

16. The disease diagnosing system according to claim 9, wherein the processor maps the plurality of the second features to the high dimensional feature space through a core function, and uses the core function to search a hyperplane in the high dimensional feature space to classify the plurality of the second features into the plurality of the categories.

* * * * *